United States Patent [19]

Pompei

[11] Patent Number: 5,031,619
[45] Date of Patent: Jul. 16, 1991

[54] METHOD FOR DETERMINING BLEEDING TIME

[75] Inventor: Francesco Pompei, Boston, Mass.

[73] Assignee: Exergen Corporation, Natick, Mass.

[21] Appl. No.: 475,789

[22] Filed: Feb. 6, 1990

[51] Int. Cl.⁵ ............................................. A61B 5/00
[52] U.S. Cl. ..................................... 128/638; 128/736
[58] Field of Search ................. 128/638, 736, 760, 770

[56] References Cited

U.S. PATENT DOCUMENTS

| | | | |
|---|---|---|---|
| 4,078,552 | 3/1978 | Chen et al. | 128/314 |
| 4,578,359 | 3/1986 | Oksman et al. | 128/638 |
| 4,583,546 | 4/1986 | Garde | 128/638 |
| 4,799,488 | 1/1989 | Mintz | 128/638 |
| 4,846,182 | 7/1989 | Fogt et al. | 128/760 |
| 4,945,919 | 8/1990 | Hattori | 128/736 |

FOREIGN PATENT DOCUMENTS

| | | | |
|---|---|---|---|
| 1333309 | 8/1987 | U.S.S.R. | 128/638 |
| 1346139 | 10/1987 | U.S.S.R. | 128/638 |

OTHER PUBLICATIONS

"Hypothermia-Induced Reversible Platelet Dysfunction", by C. R. Valeri et al., in *Ann. Surg.*, vol. 205, No. 2, Feb. 1987, pp. 175-181.

*Primary Examiner*—Lee S. Cohen
*Assistant Examiner*—Krista M. Pfaffle
*Attorney, Agent, or Firm*—Hamilton, Brook, Smith & Reynolds

[57] ABSTRACT

Apparatus for determining bleeding time includes a cutting assembly and a member for providing a compensation factor as a function of temperature of the subject. The cutting assembly provides an incision of predetermined dimensions for external bleeding therethrough. The compensation member measures temperature of the subject throughout the period of external bleeding and provides a compensation factor as a function of sensed temperature. The multiplicative product of measured time length of external bleeding and the compensation factor provide a normalized bleeding time of the subject.

4 Claims, 1 Drawing Sheet

METHOD FOR DETERMINING BLEEDING TIME

BACKGROUND OF THE INVENTION

"Bleeding time" is the time that passes before coagulation occurs in external bleeding. A measure of one's bleeding time is important for the determination of hemophilia and other blood disorders. For incisions of predetermined dimensions (length, width and depth), normal (medically acceptable) bleeding times are known and are able to be found in reference tables and the like.

Typically, a test for determining (measuring) one's bleeding time involves making an incision of a predetermined dimension and timing from a moment that bleeding through the incision begins to the moment coagulation appears to occur. Self tests are available where a cutting device for producing the incision of the predetermined dimensions is employed. The accuracy of the self test, however, is dependent at least on the ability of the cutting device to reproduce the incision of predetermined dimensions.

Another inaccuracy or complication of bleeding time tests in general concerns temperature of the subject and surrounding environment during testing. The rate at which external bleeding occurs has recently been found to be roughly inversely proportional to temperature of the subject's skin. To date, this relationship is not utilized in tests for determining bleeding time. Hence, there is a need for a method and apparatus for compensating for temperature of the subject in bleeding time tests.

SUMMARY OF THE INVENTION

The present invention provides a method and apparatus for compensating for subject temperature in tests for determining bleeding time. In particular, the present invention provides a method and apparatus for compensating for subject skin temperature in common tests for determining bleeding time.

To accomplish the foregoing objectives, the present invention provides a strip of temperature sensitive material. The temperature sensitive material is removably positioned on the subject's skin in a working area. An incision is made adjacent the strip of temperature sensitive material in the working area to cause external bleeding. The strip of temperature sensitive material is maintained positioned adjacent the incision during external bleeding through the incision. The period of time which passes during external bleeding until coagulation appears to occur is measured. Also at the moment of apparent coagulation, a reading from the strip of temperature sensitive material is made.

The strip of temperature sensitive material provides an indication of a compensation factor as a function of detected skin temperature. The indicated compensation factor at the time of the reading of the strip is used as a multiplier of the timed period of external bleeding to coagulation. The resulting quantity (i.e. product of compensation factor and timed period) provides a length of time for coagulation to occur adjusted for temperature of the subject's skin during the external bleeding. Hence, the resulting quantity provides a temperature-compensated or normalized bleeding time which is more accurate than bleeding times obtained by the prior art devices.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1a is a schematic illustration of apparatus for determining bleeding time which embodies the present invention.

FIG. 1b is a side view of a temperature compensation member of the apparatus of FIG. 1a.

FIG. 2 is a schematic illustration of use of the apparatus of FIG. 1a.

DETAILED DESCRIPTION OF THE PREFERRED EMBODIMENT

Figure 1:
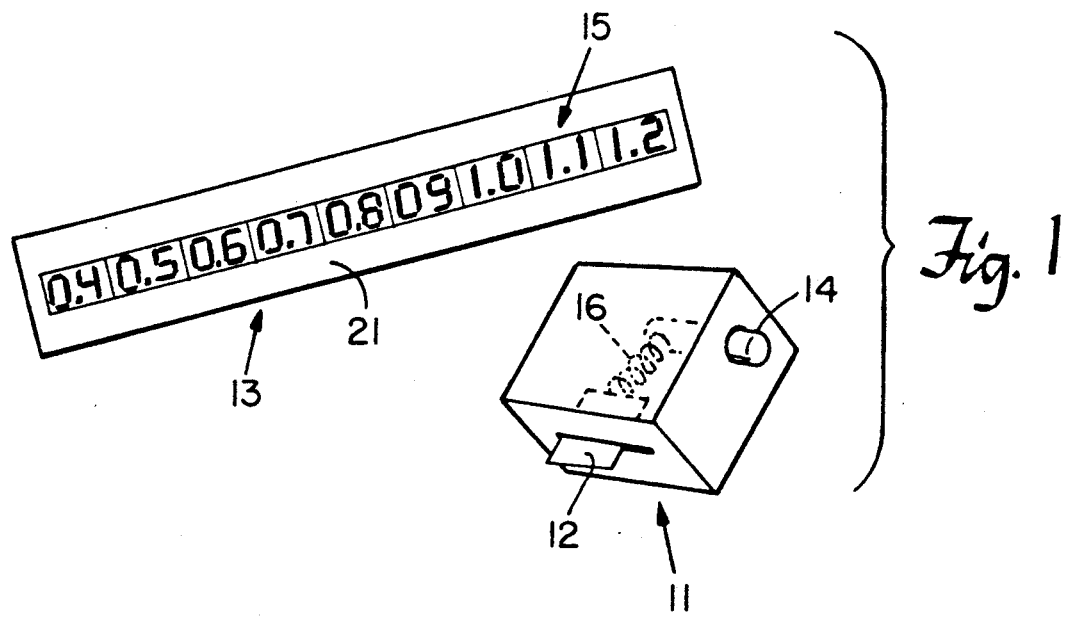

Provided in FIG. 1a is an illustration of bleed time test apparatus of the present invention. Included are a cutting assembly 11 and a temperature compensation member 13. The cutting assembly 11 enables an incision of a predetermined length, width and depth to be made in a desired working area of the subject. The cutting assembly 11 is typically a spring loaded razor blade or similar cutting edge. With release of a blade 12 by pressing of a trigger button 14, the blade is driven a predetermined distance by a spring 16. Preferably, dimensions of the incision are about 1 to 2 cm. in length, about 0.10 to about 0.5 mm in width and about 1.5 to about 2.5 mm in depth.

One such cutting assembly is the type manufactured by Organon Teknika Company, Durham, N.C. and sold under the name "Simplate II". Other such cutting assemblies as are known in the art are suitable.

The temperature compensation member 13 is formed of a strip of temperature sensitive material with a liquid crystal display 15 incorporated in one side (frontal surface 21) of the strip of material. One such strip of temperature sensitive material with a liquid crystal display on a frontal surface is described in U.S. Pat. Nos. 3,861,213; 3,898,354; and 3,965,742 all of which are herein incorporated by reference.

The display 15 of the temperature compensation member 13 is calibrated to provide a digital indication of a compensation factor between about 0.4 and 1.2 as a function of sensed temperature. The strip of temperature sensitive material when positioned, preferably with a back surface 19, on the desired working area of the subject senses temperature of the working area. The relationship between sensed temperature of the subject and compensation factor is approximately $$\text{compensation factor} = \frac{(t - 32)}{20} + 1$$

where t is sensed temperature in degrees Celsius. This relationship is based on Applicants' discovery that for every degree above or below normal temperature (32° C.) of the working area (i.e. skin of the subject), external bleeding decreases or increases respectively by a factor of about 0.05.

Figure 1B:
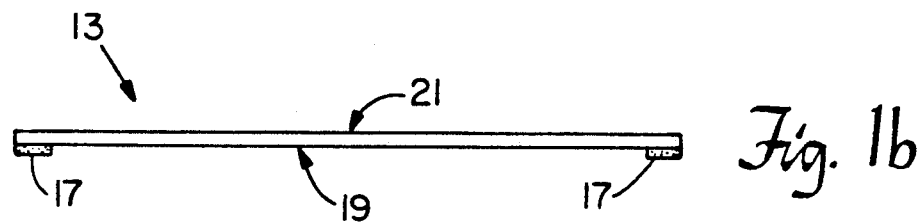

As illustrated in FIG. 1b, adhesive 17 is carried on the back surface side 19 of the end portions of the strip of temperature sensitive material. Other portions of back surface side 19 may also carry adhesive as appropriate. The adhesive 17 is of the type which allows removable adherence of the strip to a subject. Examples of such adhesives are Medical Grade Adhesive (part no. 1522) by 3M Inc.

In a preferred embodiment, the compensation member 13 has dimensions of about 2½ inches long by about ½ inch wide.

Figure 2:
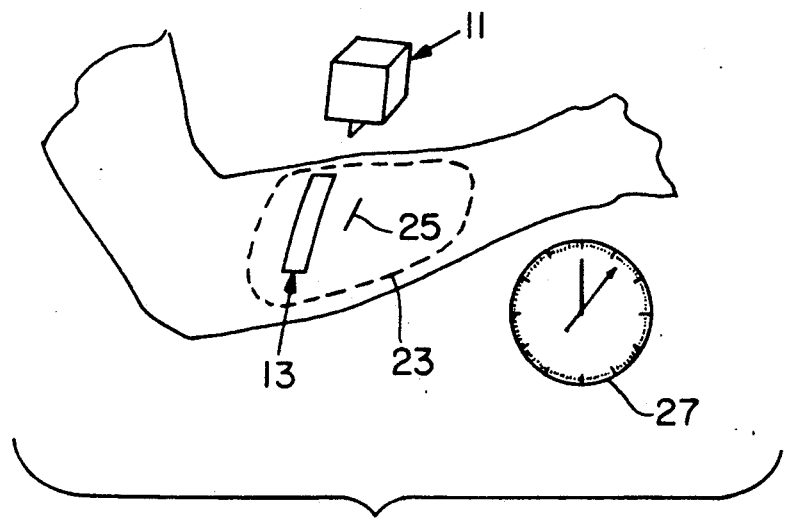

Use of the apparatus of the present invention is then as illustrated in FIG. 2. The desired working area 23 (indicated within the dotted lines) of a subject limb or other suitable body part is cleaned of any residue. The compensation member 13 is removably positioned/affixed within the working area 23 with the back surface 19 making contact with the subject's skin and the frontal surface side 21 providing display 15. The cutting assembly 11 is operated in the working area 23 near the removably positioned temperature compensation member 13 to provide an incision 25 for external bleeding of the subject. From the time that bleeding through the incision 25 occurs until coagulation of the blood from the incision is apparent, the user measures the time length of the external bleeding period by suitable means such as a clock 27.

During the period of external bleeding, temperature compensation member 13 senses localized temperature of the subject. As a function of the sensed temperature, temperature compensation member 13 indicates on its display 15 a compensation factor. At the end of the period of external bleeding (when coagulation of the blood of the incision 25 appears to occur), the user reads the display 15 of the temperature compensation member 13 to obtain a compensation factor. The obtained compensation factor and measured time length of the external bleeding period are multiplied together. The multiplicative product of the compensation factor and the measured time provide a temperature normalized bleeding time of the subject.

While the invention has been particularly shown and described with reference to a preferred embodiment thereof, it will be understood by those skilled in the art that various changes in form and details may be made therein without departing from the spirit and scope of the invention as defined by the appended claims.

I claim:

1. A method of determining bleeding time of a subject comprising the steps of:
    providing a period of external bleeding through an incision in a working area of a subject;
    determining a compensation factor as a function of temperature of the working area during external bleeding through the incision;
    measuring a length of time of the period of external bleeding from a time that bleeding through the incision in the working area begins to a time that coagulation of blood from the incision occurs; and
    normalizing the measured time length of the period of external bleeding by the determined compensation factor to provide a normalized bleeding time of the subject.

2. A method as claimed in claim 1 wherein the step of providing a period of external bleeding includes operating cutting means to create an incision in the working area.

3. A method as claimed in claim 2 wherein the step of determining a compensation factor as a function of temperature of the working area includes:
    removably positioning a layer of temperature sensitive material on the working area such that the layer senses temperature of the working area throughout the period of external bleeding; and
    at the end of the period of external bleeding, obtaining from a display coupled to a frontal surface of the layer an indication of a compensation factor defined as a function of sensed temperature.

4. A method as claimed in claim 3 wherein the step of normalizing includes multiplying the determined compensation factor and the measured time length, product of the determined compensation factor and the measured time length providing a normalized bleeding time of the subject.

* * * * *